United States Patent [19]

Detty et al.

[11] Patent Number: 5,047,419

[45] Date of Patent: Sep. 10, 1991

[54] PHOTODYNAMIC THERAPY OF GLIOMA OR MAMMARY CARCINOMA USING SELENO- OR TELLUROPYRYLIUM SALTS

[75] Inventors: Michael R. Detty, Rochester, N.Y.; Stephen K. Powers, Chapel Hill, N.C.

[73] Assignee: Eastman Kodak Company, Rochester, N.Y.

[21] Appl. No.: 261,288

[22] Filed: Oct. 24, 1988

[51] Int. Cl.$^5$ ................... A61K 31/095; A61K 31/35; A61K 31/56
[52] U.S. Cl. .................... 514/432; 514/459; 514/460; 514/180
[58] Field of Search ............... 514/184, 183, 460, 459, 514/432

[56] References Cited

U.S. PATENT DOCUMENTS 4,365,017 12/1982 Detty et al. .
4,584,258 4/1986 Detty et al. .

OTHER PUBLICATIONS

*J. Clin. Oncology*, vol. 6, p. 380 (1988).

*Primary Examiner*—Frederick E. Waddell
*Assistant Examiner*—Gregory Hook
*Attorney, Agent, or Firm*—Dana M. Schmidt

[57] ABSTRACT

There are disclosed pyrylium salts and a method of using them medicinally in photodynamic therapy for increasing the survival time of animals affected with glioma or mammary carcinoma. The salts are seleno- or telluropyrylium compounds having a singlet oxygen quantum efficiency of at least 0.005 when exposed as described at wavelengths between about 650 and 1000 nanometers.

10 Claims, No Drawings

PHOTODYNAMIC THERAPY OF GLIOMA OR MAMMARY CARCINOMA USING SELENO- OR TELLUROPYRYLIUM SALTS

FIELD OF THE INVENTION

This invention relates to novel compositions for treating glioma or mammary carcinoma cells, and a method of treatment using such compositions in phototherapy.

BACKGROUND OF THE INVENTION

Telluro- and selenopyryliums, even those very similar in structure to those described herein, have been known for use as dyes in photoconductive, photoresist and lithographic compositions or optical recording discs. See, e.g., U.S. Pat. Nos. 4,365,017 and 4,584,258, respectively. However, none of such descriptions recognized that the seleno- or telluropyrylium dyes might have a medicinal use, let alone one that is particularly effective in photodynamic therapy. To that end, the kinds of solvents and "carriers" taught for use with these known telluropyryliums have been biologically hazardous or deadly materials such as dichloromethane and bisphenol polycarbonates.

Meanwhile, the field of photodynamic therapy (pdt) has developed through the selective retention of certain dyes in localized, differentiated cancers such as differentiated carcinomas and melanoma, prior to exposure of this portion of the host to selected light energy. It has been found that dyes particularly effective in such treatment generate singlet oxygen or a superoxide anion, as reported in *J. Clinical Oncology*, Vol. 6, p. 380 (1988) and others. Because the dyes are selectively retained over time by the cancer cells, and not by the healthy cells, the ptd effect is selective also. Dyes that have been particularly recommended for this process include acridines, methylene blue, rhodamine 123, eosin, tetracycline, chlorophylls, and porphyrins such as hematoporphyrin derivatives, hereinafter HPD. The difficulty with all these conventional dye compositions used for photodynamic therapy, hereinafter pdt, has been that they absorb light primarily at wavelengths that are considerably shorter than 700 nm. In other words, they are relatively ineffective when exposed to wavelengths above 700 nm. Yet, it is well-known that light with wavelengths between about 700 and 1200 nm will readily pass through most biological tissues, unlike light of shorter wavelengths. As a result, it has been difficult to use pdt with cancers not readily accessible from the surface of the host. (Those that operate at 650 nm are still useful for surface treatment.)

Thus, prior to this invention there has been a substantial need to find cytotoxic, photoactivatable dyes that absorb primarily above 700 nm, for use i pdt.

SUMMARY OF THE INVENTION

We have discovered that certain seleno- and telluropyryliums, including some used in photoconductive and optical disc compositions of the prior art, indeed absorb light above 700 nm and then produce singlet oxygen effective to give phototherapeutic effects.

More specifically, in accord with one aspect of this invention, there is provided a composition effective to treat carcinoma or cells contained in a host mammalian body, comprising a therapeutically effective amount of a seleno- or a telluropyrylium dye having a singlet oxygen quantum efficieincy of at least 0.005, when exposed in an air-saturated solution to light of wavelengths between about 650 to 1000 nm with an energy sufficient to produce a phototherapeutic effect; and a pharmaceutically acceptable carrier.

In accord with another aspect of the invention, there is provided a method of treating glioma or mammary carcinoma cells in a host mammalian body. The method comprises administering to such host mammalian body, a therapeutically effective amount of a seleno- or a telluropyrylium dye having a singlet oxygen quantum efficiency of at least 0.005, when exposed in an air-saturated solution to light of wavelengths between about 650 to 1000 nm with an energy sufficient to produce a phototherapeutic effect; and a pharmaceutically acceptable carrier; and irradiating the site of the carcinoma or melanoma with light at the wavelengths and with the energy levels noted.

Thus, it is an advantageous feature of the invention that dyes are provided for the pdt that allow treatment anywhere in the host body, due to their ability to absorb light at wavelengths to which most of the host body is transparent.

Other advantageous features will become apparent upon reference to the following Description of the Preferred Embodiments.

DESCRIPTION OF THE PREFERRED EMBODIMENTS

We have discovered that the novel medicinal compositions of this invention, are particularly effective in phototherapy of cancer cells, most particularly fro carcinoma cells, in vivo.

The effective treatment of carcinomas described herein produces regression and/or inhibition of growth, and remission of tumors.

The invention features compositions containing telluro- or selenopyrylium dyes. Preferred are dyes having the following structural formula:

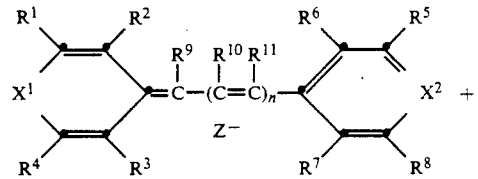

wherein $R^1$, $R^4$, $R^5$, and $R^8$ are selected from hydrogen, aryl of six to twelve carbon atoms, for example, phenyl, napththyl and the like; heteroaryl of six to twelve carbon atoms, for example, pyridyl, thienyl, furyl, etc., or alkyl of from one to twelve carbon atoms, for example methyl, ethyl, propyl, iso-propyl, butyl, t-butyl, hexyl, heptyl, octyl, dodecyl and the like; $R^2$, $R^3$, $R^6$, and $R^7$ are selected from hydrogen, amino; hydroxy; halo such as chloro, fluoro, iodo, and bromo; or alkyl, aryl or alkyl or aryl derivatives such as alkylthio, arylthio, alkoxy, alkylseleno, arylseleno, alkyltelluro or aryltelluro, all from one to twelve carbon atoms, for example, methyl, ethyl, propyl, hexyl, dodecyl, phenyl, naphthyl, methylthio, hexylthio, dodecylthio, phenylthio, the corresponding seleno equivalents of these, and the corresponding telluro equivalents of these, and the like; $R^9$, $R^{10}$, and $R^{11}$ are selected from hydrogen, halo such as chloro, fluoro, bromo and iodo; cyano; and alkyl and alkoxy of from one to twelve carbon atoms, for example methyl, ethyl, propyl, iso-propyl, butyl, t-butyl, hexyl, heptyl, octyl, dodecyl, methoxy, ethoxy, propoxy, butoxy, t-butoxy, heptoxy, dodecyloxy and the like; n is 0, 1 or 2; $X^1$ and $X^2$ are individually O, Se, S or Te except at least one is Te or Se; and Z is a water-soluble anion that is inactive with respect to the cation. As used herein, "alkyl" includes substituted alkyl, such as by hydroxy groups.

By "inactive with respect to the cation", it is meant that the anion will not add to the carbon framework of the dye to displace Se or Te from the dye. Such inctive anions include halides such as chloride, bromide and the like; tetrafluoroborate, perchlorate, mesylate, hexafluorophosphate, and the like. Excluded are anions such as hypochlorite, anions of peroxyacids, periodate, triiodide, tribromide, and any strong oxidant.

Thus, useful telluropyryliums include a salt formed by any of the aforesaid useful anions, with the pyryliums listed i Table I.

The most preferred examples of useful pyryliums include the following:

TABLE I

| Dye No. | Name |
|---|---|
| 1. | 2,6-Di-t-butyl-4-[3-(2,6-di-t-butyl-4H-telluropyran-4-ylidene)-1-propen-1-yl]selenopyrylium chloride |
| 2. | 2,6-Di-t-butyl-4-[3-(2,6-di-t-butyl-4H-selenopyran-4-ylidene)-1-propen-1-yl]selenopyrylium hexafluorophosphate |
| 2a. | 2,6-Di-t-butyl-4-[3-(2,6-di-t-butyl-4H-selenopyran-4-ylidene)-1-propen-1-yl]selenopyrylium chloride |
| 3. | 2,6-Di-t-buytl-4-[3-(2,6-di-t-butyl-4H-telluropyran-4-ylidene)-1-propen-1-yl]thiopyrylium hexafluorophosphate |
| 3a. | 2,6-Di-t-butyl-4-[3-(2,6-di-t-butyl-4H-telluropyran-4-ylidene)-1-propen-1-yl]thiopyrylium chloride |
| 4. | 2,6-Di-t-butyl-4-[3-(2,6-di-t-butyl-4H-telluropyran-4-ylidene)-1-propen-1-yl]telluropyrylium chloride |
| 5. | 2,6-Di-t-butyl-4-[3-(2,6-di-t-butyl-4H-telluropyran-4-ylidene)-1-propen-1-yl]pyrylium perchlorate |
| 6. | 2,6-Di-t-butyl-4-[3-(2,6-di-t-butyl-4H-selenopyran-4-ylidene)-3-methyl-1-propen-1-yl]telluropyrylium perchlorate |
| 7. | 2,6-Di-t-butyl-4-[3-(2,6-di-t-butyl-4H-selenopyran-4-ylidene)-1,3-dimethyl-1-propen-1-yl]selenopyrylium hexafluorophosphate |
| 8. | 2,6-Di-t-butyl-4-[3-(2,6-di-t-butyl-4H-selenopyran-4-ylidene)-1-propen-1-yl]thiopyrylium hexafluorophosphate |
| 9. | 2,6-Di-t-butyl-4-[3-(2,6-di-t-butyl-4H-selenopyran-4-ylidene)-1-propen-1-yl]pyrylium perchlorate |
| 10. | 2,6-Diphenyl-4-(2,6-diphenyl-4H-telluropyran-4-ylidenemethyl)telluropyrylium tetrafluoroborate |
| 11. | 2,6-Diphenyl-4-[1-(2,6-diphenyl-4H-telluropyran-4-ylidene)ethyl]telluropyrylium hexafluorophosphate |
| 12. | 2,6-Di-t-butyl-4-(2,6-di-t-butyl-4H-telluropyran-4-ylidenemethyl)telluropyrylium chloride |
| 13. | 2,6-Di-t-butyl-4-[1-(2,6-di-t-butyl-4H-telluropyran-4-ylidene)ethyl]telluropyrylium chloride |
| 14. | 2,6-Di-t-butyl-4-(2,6-di-t-butyl-4H-telluropyran-4-ylidenemethyl)telluropyrylium bromide |
| 15. | 2,6-Di-t-butyl-4-[3-cyano-3-(2,6-di-t-butyl-4H-telluropyran-4-ylidene)-1-propen-1-yl]telluropyrylium tetrafluoroborate |
| 16. | 2,6-Di-phenyl-4-[5-(2,6-di-phenyl-4H-telluropyran-4-ylidene)-1,3-pentadien-1-yl]telluropyrylium tetrafluoroborate |
| 17. | 2,6-Di-t-butyl-4-(2,6-di-t-butyl-4H-thiopyran-4-ylidenemethyl)-3-iodo-telluropyrylium hexafluorophosphate |

TABLE I-continued

| Dye No. | Name |
|---|---|
| 18. | 2,6-Di-(4-hydroxy-n-butyl)-4-(2,6-di-t-butyl-4H-selenopyran-4-ylidenemethyl)telluropyrylium hexafluorophosphate |

In contrast, dyes that do not work are those of the same structure, but wherein $X^1$ and $X^2$ are both either O, S, or together are O and S. Some comparative examples are set forth in Table II.

TABLE II

Comparative Examples

| C.E. No. | Name |
|---|---|
| C.E.-1 | 2,6-Di-t-butyl-4-[3-(2,6-di-t-butyl-4H-thiopyran-4-ylidene)-1-propen-1-yl]thiopyrylium hexafluorophosphate |
| C.E.-2 | 2,6-Di-t-butyl-4-[3-(2,6-di-t-butyl-4H-thiopyran-4-ylidene)-1-propen-1-yl]pyrylium hexafluorophosphate |
| C.E.-3 | 2,6-Di-t-butyl-4-[3-(2,6-di-t-butyl-4H-pyran-4-ylidene)-1-propen-1-yl]pyrylium chloride |

SYNTHESIS

Any useful synthesis can be applied to make the dyes used in the composition of the invention. Some techniques are indicated in the aforesaid U.S. Pat. No. 4,365,017. Except for those in which the anion Z is a Lewis base (see examples hereinafter) and $X^1$ and $X^2$ are different, the following general procedures are useful:

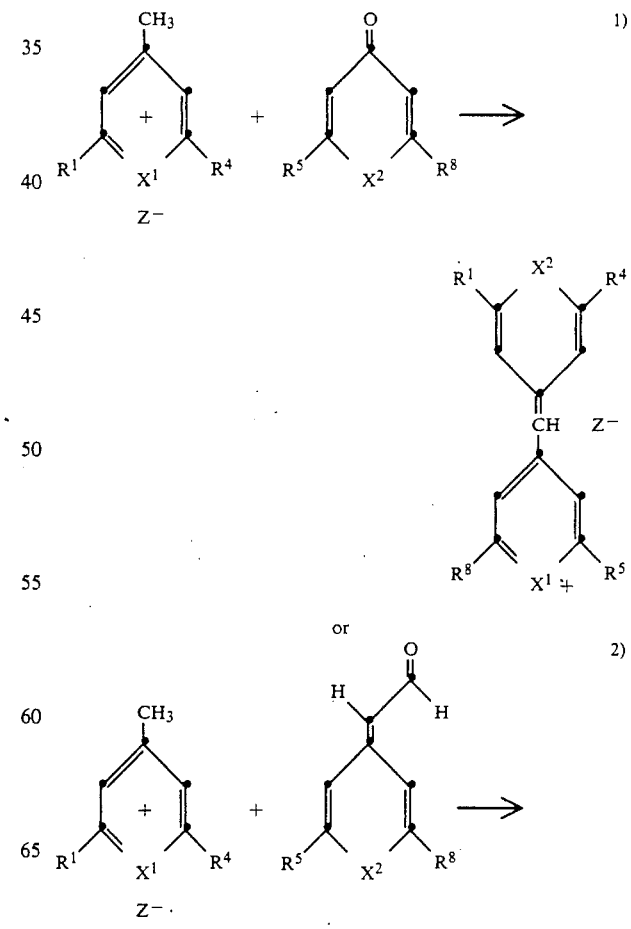

-continued

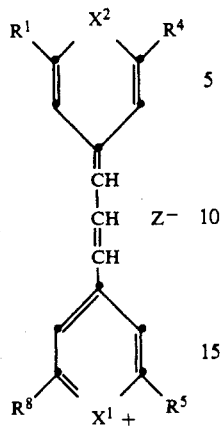

wherein Z is the desired anion, $X^1$ and $X^2$ are the desired chalcogenide, and $R^1$, $R^4$, $R^5$, and $R^8$ are the desired substituents on the rings.

However, if Z is to be a Lewis base, for example halide or mesylate and $X^1$ and $X^2$ are to be different, then in order to obtain a pharmaceutically pure dye, it is necessary to use the procedure described and claimed in related U.S. application Ser. No. 261,289 co-filed herewith by Michael Detty entitled "Mixed Chalcogenide Pyrylium Salts of a Lewis Base", now U.S. Pat. No. 4,916,127. That procedure comprises taking the desired dye with an anion that is not a Lewis base anion, mixing such a salt with ion exchange resin containing a Lewis base, and allowing an ion exchange to occur. In addition, this procedure can be used to prepare a Lewis base salt of even those dyes in which $X^1$ and $X^2$ are identical.

PREPARATION EXAMPLES

Preferred dyes were prepared by either of the two following general reactions:

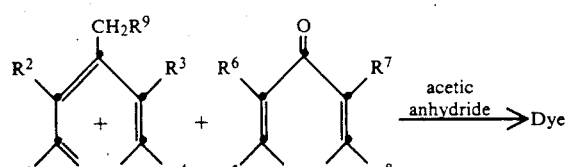

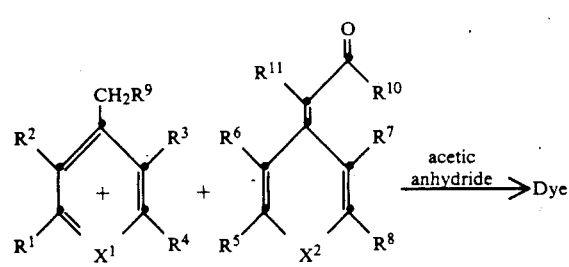

wherein $R^1$-$R^{11}$, $X^1$, $X^2$, n, and Z (except for Z=Cl, Br or $CH_3SO_3^-$) are chosen as described above. For preparation of dyes containing Z=Cl, Br or $CH_3SO_3^-$, an ion exchange resin was employed with the tetrafluoroborate, hexafluorophosphate, or perchlorate salt of the dye.

PREPARATION 1 OF THE CHLORIDE SALT OF DYE 1

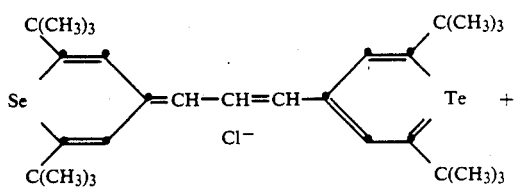

The perchlorate salt of Dye 1 (0.19 g; 0.27 mmol) and 1.5 g of AMBERLITE IRA-400 (Cl) ion exchange resin available from Rohn & Haas Co. were stirred in 75 mL of methanol for 4 hours. The ion exchange resin was removed by filtration and the filter cake was washed with 10 mL of methanol. The combined filtrates were stirred for an additional 2 hours with 1.5 g of the ion exchange resin. The ion exchange resin was removed by filtration and the filter cake was washed with 10 mL of methanol. The combined filtrates were concentrated in vacuo. The residue was dissolved in 5 mL of acetonitrile which was then diluted with ether to 50 mL. Chilling precipitated the dye as yellow-green crystals which were collected by filtration, washed with ether, and dried to give 0.14 g (82%) of the dye, mp 213.5°–215° C. $\lambda_{max}$ ($CH_2Cl_2$) 786 nm ($\epsilon$304,000). $^1$H NMR ($CD_3OD$) $\delta$8.87 (t, 1H, J=13.3 Hz), 7.78 (br s, 4H), 6.76 (d, 1H, J=13.3 Hz), 6.71 (d, 1H, J=13.3 Hz), 1.47 (s, 27H), 1.45 (s, 9H). Anal. Calcd for $C_{29}H_{43}SeTe.Cl$: C, 55.0; H, 6.8; Cl, 5.6. Found: C, 55.2; H, 6.8; Cl, 5.5.

PREPARATION 2 OF THE CHLORIDE SALT OF DYE 2A

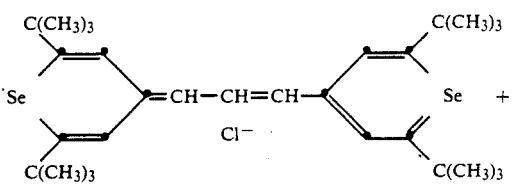

The hexafluorophosphate salt of Dye 2 (0.11 g, 0.20 mmol) was dissolved in 10 mL of methanol. 2.0 g of AMBERLITE IRA-400 (Cl) ion exchange resin was added and the resulting mixture was stirred for one hour at ambient temperature. The resin was removed by filtration and the filter cake was washed with 5 mL of methanol. The combined filtrates were concentrated. The residue was recrystallized from 1 mL of acetonitrile and 20 mL of ether to give 0.053 g (50%) of Dye 2a. mp 209°–209.5° C. $\lambda_{max}$ (water) 730 nm ($\epsilon$300,000). $^1$H NMR ($CD_3OD$) $\delta$8.78 (t, 1H, J=13 HZ), 7.75 (br s, 4H), 6.67 (d, 2H, J=13 Hz), 1.46 (s, 36H). Anal. Calcd for $C_{29}H_{43}Se_2$: C, 59.5; H, 7.4; Cl, 6.1. Found: C, 59.6; H, 7.5; Cl, 7.1.

PREPARATION 3 OF THE CHLORIDE SALT OF DYE 3A

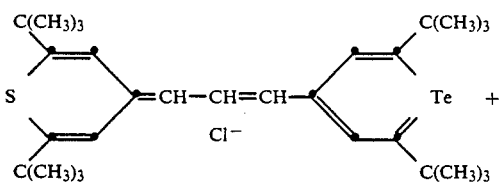

The hexafluorophosphate salt of Dye 3 (0.070 g, 0.10 mmol) was dissolved in 20 mL of methanol. One gram of the AMBERLITE IRA-400 (Cl) ion exchange resin was added. The resulting mixture was stirred at ambient temperature for four hours. The ion exchange resin was removed by filtration and the filter cake was washed with 10 mL of methanol. The combined filtrates were concentrated. The residue was recrystallized from 1 mL of acetonitrile and 20 mL of ether. Chilling precipitated copper bronze needles of the dye which were collected by filtration, washed with ether, and dried to give 0.048 g (81%) of Dye 3a. mp 200.2°–203.5° C. $\lambda_{max}$ (water) 745 nm (e110,000). $^1$H NMR (CD$_3$OD) δ8.77 (t, 1H, J=13 Hz), 7.93 (br s, 2H), 7.7 (br s, 2H), 6.69 (d, 2H, J=13Hz), 1.48 (s, 18H), 1.42 (s, 18H). Anal. Calcd for C$_{29}$H$_{43}$STeCl: C, 59.4; H, 7.4; Cl, 6.0. Found: C, 59.3; H, 7.4; Cl, 5.8.

COMPARATIVE PREPARATION EXAMPLE—ATTEMPTED PREPARATION OF THE CHLORIDE SALT OF DYE 1 WITH CONDENSATION TECHNOLOGY 2,6-Di-tert-butyl-4-methylselenopyrylium chloride (6.00 g, 18.8 mmol) and (2,6-di-tert-butyltelluropyran-4-ylidene)acetaldehyde (6.72 g, 19.4 mmol) in 20 mL of acetic anhydride were heated on a steam bath for eleven minutes. The reaction mixture was cooled to ambient temperature and 15 mL of acetonitrile was added. The resulting solution was filtered through a pad of glass wool. The filtrate was diluted with 250 mL of ether and the resulting solution was chilled. The dye precipitated as copper-bronze crystals which were collected by filtration, washed with ether, and dried to give 10.51 g (88%) of the dye. $^1$H NMR and absorption spectroscopies showed the product to be a one to two to one mixture of Dye 2 to Dye 1 to Dye 4, respectively. This mixture is expected from a statistical distribution of the heteroatoms if random scrambling of the heteroatoms were to occur during reaction. It still has a pdt utility, but such a mixture requires FDA approval on each component separately as well as in combination, an undesirable expense for a result that is most likely to be less satisfactory than the results from a pharmaceutically pure dye. ("Pharmaceutically pure" means, the dye has 2 wt % or less impurities, the standard set by the FDA.)

UTILITY EXAMPLE

In the pdt method of treating differentiated carcinomas or melanoma in mammals, the dye is particularly useful when added to a pharmaceutically acceptable carrier. The pharmaceutically acceptable carrier can be selected from a variety of carriers, such as a solvent that will sufficiently dissolve the pyrylium dye. Among preferred examples of a suitable carrier solvent is a minimal amount (100 mg of dye in 1 mL of 95% ethanol) diluted with phosphate buffered saline to produce a dye salt concentration of 1 mM. Still other useful examples include a 5% dextrose solution in water, or a mixture of ethanol and a polyol such as polyethoxylated caster oil, available from the National Cancer Institute as "Diluent No. 12."

Still other acceptable carrier solvents include, dimethyl sulfoxide (DMSO) for intravesical treatment, and isotonic saline for IV and IP injections.

Still other carriers that are useful include the following:

Materials such as gelatin, natural sugars such as sucrose or lactose, lecithin, pectin, starch (for example cornstarch), alginic acid, tylose, talc, lycopodium, silica (for example colloidal silica), glucose cellulose, cellulose derivatives, for example cellulose ethers in which the cellulose hydroxyl groups are partially etherified with lower aliphatic alcohols and/or lower saturated oxyalcohols (for example, methyl hydroxypropyl cellulose, methyl cellulose, hydroxyethyl cellulose), stearates, e.g., methyl stearate and glyceryl stearate, magnesium and calcium salts of fatty acids with 12 to 22 carbon atoms, especially saturated acids (for example, calcium stearate, calcium laurate, magnesium oleate, calcium palmitate, calcium behenate and magnesium stearate), emulsifiers, oils and fats, especially of plant origin (for example, peanut oil, castor oil, olive oil, sesame oil, cottonseed oil, corn oil, wheat germ oil, sunflower seed oil, cod-liver oil), mono-, di-, and triglycerides of saturated fatty acids ($C_{12}H_{24}O_2$ to $C_{18}H_{36}O_2$ and their mixtures), e.g., glyceryl monostearate, glyceryl distearate, glyceryl tristearate, glyceryl trilaurate), pharmaceutically compatible mono-, or polyvalent alcohols and polyols such as glycerine, mannitol, sorbitol, pentaerythritol, ethyl alcohol, diethylene glycol, triethylene glycol, ethylene glycol, propylene glycol, dipropylene glycol, poly(ethylene glycol), and other poly(alkylene glycols), as well as derivatives of such alcohols and polyglycols, esters of saturated and unsaturated fatty acids (2 to 22 carbon atoms, especially 10 to 18 carbon atoms), with monohydric aliphatic alcohols (1 to 20 carbon atom alkanols), or polyhydric alcohols such as glycols, glycerine, diethylene glycol, pentaerythritol, sorbitol, mannitol, ethyl alcohol, butyl alcohol, octadecyl alcohol, etc., e.g., glyceryl stearate, glyceryl palmitate, ethylene distearate, ethylene dilaurate, ethylene diacetate, monoacetin, triacetin, glyceryl oleate, esters of polyvalent alcohols that are etherified, benzyl benzoate, dioxolane, glycerin formal, tetrahydrofurfuryl alcohol, polyglycol ethers of 1 to 12 carbon atom alcohols, lactamide, lactates, e.g., ethyl lactate, ethyl carbonate, silicones (especially medium viscosity dimethyl polysiloxane), magnesium carbonate and the like.

Still other additives, and methods of preparation of the compositions, can be found in the extant literature.

Useful methods of delivery of the dye and carrier include intravenous (IV), intraperitoneal (IP) intravesical, and arterial injection.

The dosage levels depend upon which pyrylium dye is being used on which cancer. Such dosage may be determined by one skilled in the art, using the techniques described in Goodman and Gilman's "The Pharmacological Basis of Therapeutics" (6th edition), pages 1675–1737, subtitled "Design and Optimization of Dosage Regimens" (Macmillan Publishing Co., New York, 1980). Based on dosages commonly experienced for pdt agents, and the correlation that has been shown between clinical tests and the LD$_{50}$ dosages found in animal protocols, it is estimated the dosages for human consumption would be: 1.0 to 7.5 mg/kg of body weight, using various injection protocols that do not exceed this level, followed by phototherapy within an appropriate time as explained in the examples hereinafter.

The ability of the dyes of this invention to function as a cancer-treating agent is in part a reflection of the effective in killing cancer cells because of their high quantum efficiency, but also they generally operate at the most preferred wavelengths, namely those of 700 nm or longer. Table III contains examples of chalcogenopyrylium dyes, their quantum efficiencies for singlet oxygen generation, and their absorption maxima. (In this Table, Ph=Phenyl, Me=Methyl, and t-Bu=-tertiary butyl.)

TABLE III

Quantum Efficiencies of Singlet Oxygen Generation ($\Phi$) and Absorption Maxima ($\lambda_{max}$) for Chalcogenopyrylium Dyes $$\text{Structure with } R^1, X^1, R^2, R^3, R^4, R^5, X^2, Z^-, n$$

| Dye | $X^1$ | $X^2$ | $R^1$ | $R^2$ | $R^3$ | $R^4$ | $R^5$ | n | Z | $\Phi(^1O_2)$ | $\lambda_{max}$ | (solvent) |
|---|---|---|---|---|---|---|---|---|---|---|---|---|
| 1 | Te | Se | t-Bu | H | H | H | H | 1 | Cl | 0.09 | 786 nm | ($CH_2Cl_2$) |
| 2 | Se | Se | t-Bu | H | H | H | H | 1 | $PF_6$ | 0.014 | 730 nm | ($H_2O$) |
| 3 | Te | S | t-bu | H | H | H | H | 1 | $PF_6$ | 0.07 | 745 nm | ($H_2O$) |
| 4 | Te | Te | t-Bu | H | H | H | H | 1 | Cl | 0.13 | 830 nm | ($CH_2Cl_2$) |
| 5 | Te | O | t-Bu | H | H | H | H | 1 | $ClO_4$ | 0.06 | 700 nm | ($H_2O$) |
| 6 | Se | Te | t-Bu | Me | H | H | H | 1 | $ClO_4$ | 0.01 | 803 nm | ($CH_2Cl_2$) |
| 7 | Se | Se | t-Bu | Me | H | Me | H | 1 | $PF_6$ | 0.005 | 790 nm | (MeOH) |
| 8 | Se | S | t-bu | H | H | H | H | 1 | $PF_6$ | 0.008 | 700 nm | ($H_2O$) |
| 9 | Se | O | t-Bu | H | H | H | H | 1 | $ClO_4$ | 0.005 | 660 nm | ($H_2O$) |
| 10 | Te | Te | Ph | H | — | — | H | 0 | $BF_4$ | 0.08 | 760 nm | (MeOH) |
| 11 | Te | Te | Ph | Me | — | — | H | 0 | $PF_6$ | 0.01 | 843 nm | ($CH_2Cl_2$) |
| 12 | Te | Te | t-Bu | H | — | — | H | 0 | Cl | 0.07 | 705 nm | ($H_2O$) |
| 13 | Te | Te | t-bu | Me | — | — | H | 0 | Cl | 0.005 | 790 nm | ($H_2O$) |
| 14 | Te | Te | t-Bu | H | — | — | H | 0 | Br | 0.07 | 705 nm | ($H_2O$) |
| 15 | Te | Te | t-Bu | CN | H | H | H | 1 | $BF_4$ | 0.08 | 790 nm | (MeOH) |
| 16 | Te | Te | Ph | H | H | H | H | 2 | $BF_4$ | 0.005 | 1060 nm | (MeOH*) |
| 17 | Te | S | [See Table I] | H | H | H | I | 0 | $PF_6$ | 0.04 | 655 nm | (MeOH) |
| 18 | Se | Te | [See Table I] | H | — | — | H | 0 | $PF_6$ | at least 0.005** | 690 nm | (MeOH) |

*This compound tended to be unstable in solution; however, other moieties as $R^1$ may produce better stability.
**Estimated.

ability of the dye to generate singlet oxygen in air-saturated solution. (As used herein, "air-saturated solution" means a solution of dye exposed to the atmosphere.) In studying a variety of chalcogenopyrylium dyes, only those dyes containing a selenium or tellurium atom show any appreciable generation of singlet oxygen upon irradiation. Fortuitously, selenopyrylium and telluropyrylium dyes have absorption maxima that are shifted to the red relative to their pyrylium and thiopyrylium analogues. That is, not only are these dyes All of these have a $\Phi$ value that is at least 0.005. In contrast, the $\Phi$ value for the comparative examples of Table IV is less. Also, $\lambda_{max}$ of Table III is in each case 650 nm or higher, and in most cases above 700 nm.

TABLE IV

Quantum Efficiencies of Singlet Oxygen Generation ($\Phi$) and Absorption Maxima ($\lambda_{max}$) for Chalcogenopyrylium Dyes

| Dye | $X^1$ | $X^2$ | $R^1$ | $R^2$ | $R^3$ | $R^4$ | n | Z | $\Phi(^1O_2)$ | $\lambda_{max}$ | (solvent) |
|---|---|---|---|---|---|---|---|---|---|---|---|
| C.E. 1 | S | S | t-Bu | H | H | H | 1 | $PF_6$ | $\leq 0.001$ | 660 nm | ($H_2O$) |
| C.E. 2 | S | O | t-Bu | H | H | H | 1 | $PF_6$ | $\leq 0.001$ | 630 nm | ($H_2O$) |
| C.E. 3 | O | O | t-Bu | H | H | H | 1 | Cl | $\leq 0.001$ | 595 nm | ($H_2O$) |

It should be noted also that $\lambda_{max}$ of these comparative examples is below 700 nm in each case.

The amount of light exposure needed for the pdt is generally on the order of at least about 15 Joules/$cm^2$, if the wavelengths used are 700 nm or above, that is, the wavelengths effective to penetrate most body tissues. Increased amounts are useful if the dye has a value of Φ of only 0.005 or slightly larger. The wavelength of exposure should be picked to match $\lambda_{max}$. Preferred methods of exposure include lasers such as conventional argon-pumped dye lasers using, for example, laser dye LDS 751, or laser diodes with a fixed wavelength of >700 nm, e.g., 800±2 nm, coupled by a 400 μm quartz fiber optic. Also useful are tungsten lights with cut-off filters that block light below 730 nm.

EXAMPLES

The following examples illustrate the effectiveness of this invention in treating the noted cancers.

EXAMPLES 1-12

In Vitro Testing of Glioma, Melanoma and Squamous Cell Carcinoma

Several selenopyrylium dyes and telluropyrylium dyes from Table I that generated singlet oxygen upon irradiation in air-saturated methanol were examined in vitro in mammalian cell cultures for their effectiveness as agents for photodynamic therapy. These results are compiled in Table V. The cell lines that were examined include U251 (human glioma), B-16 melanoma (mouse melanoma), and FADU (human squamous cell carcinoma). As controls, HSK1 (normal human skin fibroblasts) and CV-1 (normal monkey kidney cells) were used.

In vitro cell cultures were grown in antibiotic-free growth medium DMEM-F12 supplemented to 10% with fetal bovine serum and adjusted to 4.5 mM with L-glutamine. DMEM-F12 is a 1:1 mixture of Dulbecco's modified Eagle's medium (Gibco) and Ham's nutrient mixture F12 (Gibco). Prior to cell seeding, multiwell plates were blackened with spray paint, coating the external walls of each well to minimize light scattering from well to well. Subconfluent cell cultures were trypsinized and plated at a concentration of $10^5$ cells per 2 $cm^2$ well. Cells were allowed to incubate overnight at 37° C. in a humidified atmosphere before dye and/or light exposure.

Stock solutions of the chalcogenopyrylium dyes were prepared at 1 mM concentration by sonication in 95% ethanol in the dark. These stock solutions were diluted with growth medium to the desired concentration. Dyes were protected from light throughout the entire experimental procedure until the time for irradiation. Standard treatment time for dye exposure was 1 hour. The dye containing medium was replaced with fresh growth medium prior to irradiation. Eighteen to twenty-four hours later, the remaining metabolically active cells were evaluated by the MTT colorimetric assay and/or cell counting. Assays were performed in triplicate with standard deviations generally of less than 10%. Percent kill was determined from mean optical density of the treated samples and that of the control (untreated) samples for the MTT analysis and from mean cell counts for these two groups for the cell-counting method. (See Table V).

Near-infrared and visible light from three sources were employed in these assays. Tungsten light (100–200 mW) was used to assess low milliwatt multiple wavelength effects. An argon-pumped dye laser (Model 150 Aurora, Cooper Lasersonics, Inc., Santa Clara, Calif.) with laser dye LDS 751 (Exciton Chemical Co., Inc., Dayton, Ohio) and a peak wavelength of 785±5 nm was coupled by a 1 μm quartz fiberoptic to a microlens assembly that gave a uniform mode of distribution of light intensity. Thirdly, a laser diode (Model 2430-H2, Spectra Diode Laboratories, Inc., San Jose, Calif. with a fixed wavelength of 800±2 nm provided light energy in the near infrared. The diode was coupled by a 400 μm quartz fiberoptic with a clear and polished end. For laser irradiation experiments, the distance of the fiber tip from the well bottom was adjusted so that the laser irradiation exactly covered the 2 $cm^2$ target area. A distal power meter (Model 2000, Coherent, Inc., Auburn, Calif.) was used to determine the energy output of the laser source.

TABLE V

In Vitro Testing of Selenopyrylium and Telluropyrylium Dyes as Photosensitizers for Photodynamic Therapy in Mammalian Cells

| Ex. No. | Dye | Z | Concentration, M | Cell Line[a] | Total Energy J $cm^{-2}$ | % Surviving Fraction Dark | % Surviving Fraction Light | Light Source[b] |
|---|---|---|---|---|---|---|---|---|
| Control 1 | 1 | Cl | $5 \times 10^{-8}$ | HSK1 | 15 | 99.0 | 97.0 | C |
| Control 2 | 1 | Cl | $5 \times 10^{-8}$ | CV1 | 15 | 100.0 | 99.0 | A |
| 1 | 1 | Cl | $5 \times 10^{-8}$ | U251 | 15 | 85.0 | 65.0 | C |
| 2 | 1 | Cl | $5 \times 10^{-8}$ | B-16 | 15 | 99.0 | 0.03 | A |
| 3 | 1 | Cl | $5 \times 10^{-8}$ | FADU | 15 | 99.0 | 0.1 | A |
| Control 3 | 5 | Cl | $1 \times 10^{-7}$ | HSK1 | 15 | 99.0 | 99.0 | A |
| Control 4 | 5 | Cl | $1 \times 10^{-7}$ | CV1 | 15 | 100.0 | 99.0 | A |
| 4 | 5 | Cl | $1 \times 10^{-7}$ | U251 | 15 | 90.0 | 58.0 | A |
| 5 | 5 | Cl | $1 \times 10^{-7}$ | B-16 | 15 | 99.0 | 0.1 | A |
| 6 | 5 | Cl | $1 \times 10^{-7}$ | FADU | 15 | 99.0 | 0.05 | A |
| Control 5 | 9 | Cl | $1 \times 10^{-6}$ | CV1 | 15 | 100.0 | 99.0 | A |
| 7 | 9 | Cl | $1 \times 10^{-6}$ | B-16 | 15 | 99.0 | 0.2 | A |
| 8 | 9 | Cl | $1 \times 10^{-6}$ | FADU | 15 | 99.0 | 0.2 | A |
| Con | 4 | $BF_4$ | $1 \times 10^{-6}$ | CV1 | 50 | 99.0 | 95.0 | A |

TABLE V-continued

In Vitro Testing of Selenopyrylium and
Telluropyrylium Dyes as Photosensitizers for
Photodynamic Therapy in Mammalian Cells

| Ex. No. | Dye | Z | Concentration, M | Cell Line[a] | Total Energy J cm$^{-2}$ | % Surviving Fraction Dark | % Surviving Fraction Light | Light Source[b] |
|---|---|---|---|---|---|---|---|---|
| trol 6 | | | | | | | | |
| 9 | 4 | BF$_4$ | 1 × 10$^{-6}$ | U251 | 50 | 100.0 | 75.0 | B |
| 10 | 4 | BF$_4$ | 1 × 10$^{-6}$ | B-16 | 27 | 99.0 | 30.0 | A |
| Control 7 | 12 | Cl | 1 × 10$^{-7}$ | HSK1 | 50 | 100.0 | 99.0 | A |
| 11 | 12 | Cl | 1 × 10$^{-7}$ | U251 | 50 | 83.0 | 74.0 | A |
| 12 | 12 | Cl | 1 × 10$^{-6}$ | U251 | 50 | 55.0 | 1.0 | A |
| Control 8 | CE-3 | Cl | 1 × 10$^{-6}$ | CV1 | 27 | 100.0 | 99.0 | D |
| Comp. Ex. | CE-3 | Cl | 1 × 10$^{-6}$ | B-16 | 27 | 99.0 | 99.0 | D |
| Comp. Ex | CE-3 | Cl | 1 × 10$^{-6}$ | FADU | 27 | 99.0 | 99.0 | D |

[a] HSK1, normal human skin fibroblasts; CV1, normal monkey kidney cells; U251, human glioma; B-16, mouse melanoma; FADU, human squamous cell.
[b] A, tungsten light source with at cutoff filter at approximately 730 nm; B, dye laser with emission maximum a 785 ± 5 nm; C, diode laser with emission at 800 ± 2 nm; D, tungsten light source with a cutoff filter at 500 nm.

It can be seen from Table V that most of the cancer cells in question were effectively killed by the dyes of the invention, but only after exposure to the light energy. (At least a 5% reduction in survival after light exposure is needed, beyond the survival level in the dark, to establish a phototherapeutic effect.)

EXAMPLES 13-14

In Vivo Drug Delivery Against Glioma

Dye 1 of Table 1 was delivered to glioma sites in rat brains, such sites having been achieved by implanting RT-1 rat glioma cancer cells into the brains of twenty-four 400 g rats. Stock solutions of Dye 1 at 1 mM concentration were prepared by dissolving the dye in a minimal amount of 95% ethanol and diluting with phosphate buffered saline to 1 mM. RT-1 glioma cells were injected into the cortex of the rats at day 0. Treatment with the dye was done at day 12. A quantity of the stock solution sufficient to deliver 1.5 mg (2.5 μmol) of Dye 1 per rat (approximately 2 mL) was delivered by femoral artery or carotid artery injection. The animals were sacrificed at the indicated times, the indicated tissues were removed, and frozen until the amount of dye was quantified. The dye content of the indicated tissues was examined spectroscopically by homogenizing the tissues, doing a lipid extraction of the homogenate, and measuring the optical density of the extract at a constant volume at the wavelength of the dye. Alternatively, a tritium labeled sample of Dye 1 was employed in the injection and the tissue homogenate was placed directly in a scintillation vial. The dye content was then measured by tritium count. These data are compiled in Table VI. (The values listed at times of 0.25 and 1.0 h after injection are comparative examples only, since there is either too high a concentration present in the brain, or too little in the tumor.)

From the data in Table VI, reasonably high concentrations of the dye in the tumor mass can be obtained at short time periods following injection. The dye appears to pass the blood-brain barrier in this particular animal model. "Brain" as used in Table VI refers to normal brain cells, and "tumor" refers to tumor cells.

TABLE VI

Distribution of Dye 1 in Organ Tissues of Tumor Bearing Rats

| Ex. No. | Injection Site | μM of Dye 1 | Time Post-Injection | Organ | Methodology Sample Prep.[a] | Methodology Anal Method[b] | nmol Dye 1/g of tissue |
|---|---|---|---|---|---|---|---|
| Comp. Ex. | Femoral Artery | 2.5 | 0.25 h | Brain | D | A | 46 |
| Comp. Ex. | Femoral Artery | | | Tumor | D | A | 45 |
| Comp. Ex. | Femoral Artery | | | Liver | D (H) | A (A) | 9.1 (5.4) |
| Comp. Ex. | Femoral Artery | | | Heart | D | A | 7.4 |
| Ex. 13 | Femoral Artery | | 0.50 h | Brain | D | A | 18.0 |
| Ex. 13 | Femoral Artery | | | Tumor | D | A | 32.0 |
| Ex. 13 | Femoral Artery | | | Liver | D | A | 17.0 |
| Comp. Ex. | Femoral Artery | | 1.0 h | Brain | D | A | 4.7 |
| Comp. | Femoral | | | Tumor | D | A | 0.0 |

TABLE VI-continued

| Ex. No. | Injection Site | μM of Dye 1 | Time Post-Injection | Organ | Methodology Sample Prep.[a] | Anal Method[b] | nmol Dye 1/g of tissue |
|---|---|---|---|---|---|---|---|
| Ex. Comp. | Femoral Artery | | | Heart | D (L) | A (B) | 1.3 (1.1) |
| Ex. Comp. | Femoral Artery | | | Liver | D (L) | A (B) | 13.2 (3.3) |
| Ex. 14 | Carotid Artery | 2.5 | 0.33 h | Brain | H | A | 0.9 |
| Ex. 14 | Carotid Artery | | | Tumor | H | A | 16.0 |

[a]For sample preparation: H, homogenate of tissue used directly; D, the homogenate was digested using hydrogen peroxide and PCA; L, lipid extraction of the homogenate.
[b]For analysis method: A, tritium counts; B, spectrophotometric measurement of optical density.

These examples demonstrate that, by this arterial delivery, optimum times for exposure for glioma cancer in the brain were from about 0.35 to about 0.5 hours after injection, since at that time most of the drug had left the normal cells but was still retained by the cancer cells.

EXAMPLE 15

In Vivo Delivery Against Mammary Carcinoma

Similar results were obtained using Dye 5 as the chloride salt, with 250 g rats bearing an implanted mammarian tumor. See Table VII.

TABLE VII

| Ex. No. | Injection Site | μM of Dye 1 | Time Post-Injection | Organ | Methodology Sample Prep.[a] | Anal Method[b] | nmol Dye 1/g of tissue |
|---|---|---|---|---|---|---|---|
| 15 | Peritoneum | 2.5 | 2 h | Tumor | L | B | 5.5 |
| 15 | " | | | Liver | L | B | 4.1 |
| | | | | Heart | L | B | 1.3 |
| | | | | Kidney | L | B | ≦0.5 |
| Comp. Ex. | | | 4 h | Tumor | L | B | 3.3 |
| | | | | Liver | L | B | 3.8 |
| | | | | Heart | L | B | ≦0.5 |
| | | | | Kidney | L | B | ≦0.5 |

[a]For sample preparation: H, homogenate of tissue used directly; D, the homogenate was digested using hydrogen peroxide and PCA; L, lipid extraction of the homogenate.
[b]For analysis method: A, tritium counts; B, spectrophotometric measurement of optical density.

EXAMPLE 16

Effectiveness of Drug Against Glioma, In Vivo

A survival study was conducted using Dye 1 with 400 g rats implanted with RT-1 glioma cells at day 0 and treated with 2.5 μmol of dye delivered by femoral artery injection on day 12. The treated animals were irradiated one hour post injection using a quartz fiber optic with a diffusion tip with the dye laser described earlier as the light source. Total irradiation energy was 50 J cm$^{-2}$ at 785 nm. Three control groups were used: untreated animals, animals treated with dye only, and animals treated with light only. [The number of rats per group were: 10 for laser and dye treatment, 6 for control (no treatment), 14 for dye only and 6 for laser only.] Mean survival time data are compiled in Table VIII. Table IX presents the number of surviving animals as a function of time. From the data in Tables VIII and IX, animals treated with Dye 1 and light show prolonged survival relative to animals in the control groups.

TABLE VIII

| | Mean Survival Time (Days) by Group | | | |
|---|---|---|---|---|
| Treatment | Laser + Dye | Control | Dye Only | Laser Only |
| Mean[a] | 32.8 | 25.3 | 27.9 | 25.5 |

[a]Mean survival time in days.

TABLE IX

| | Proportion of Animals Surviving by Day | | | |
|---|---|---|---|---|
| Treatment Day No.[a] | Laser + Dye | Control | Dye Only | Laser Only |
| ≧15 | 0.70 | 0.50 | 0.50 | 0.67 |
| ≧19 | 0.70 | 0.50 | 0.43 | 0.50 |
| ≧22 | 0.70 | 0.33 | 0.43 | 0.33 |
| ≧26 | 0.60 | 0.33 | 0.43 | 0.33 |
| ≧33 | 0.50 | 0.33 | 0.43 | 0.33 |
| ≧40 | 0.50 | 0.33 | 0.43 | 0.33 |
| ≧47 | 0.30 | 0.00 | 0.00 | 0.00 |

[a]Day 0 is day of tumor cell implantation. Treatment was at Day 12.

As will be readily apparent, from day 47 on, all the control animals were dead, while 30% of the animals being fully treated were still alive.

The invention has been described in detail with particular reference to preferred embodiments thereof, but it will be understood that variations and modifications can be effected within the spirit and scope of the invention.

What is claimed is:

1. A composition effective for increasing the survival time of animals affected with glioma or mammary carcinoma cells, comprising a therapeutically effective amount of a seleno- or a telluropyrylium dye having a singlet oxygen quantum efficiency of at least 0.005, when exposed in an air-saturated solution to light of wavelengths between about 650 to 1000 nm with an energy sufficient to produce a phototherapeutic effect; and a pharmaceutically acceptable carrier.

2. A composition as defined in claim 1, wherein said dye has the following structural formula:

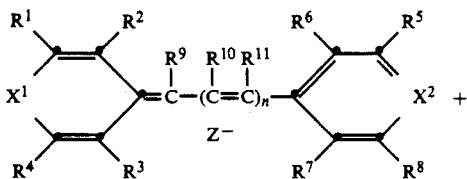

wherein $R^1$, $R^4$, $R^5$, and $R^8$ are selected from hydrogen, aryl, or alkyl from one to twelve carbon atoms; $R^2$, $R^3$, $R^6$, and $R^7$ are selected from hydrogen, alkyl, aryl, alkylthio, arylthio, alkoxy; alkylseleno, arylseleno, alkyltelluro or aryltelluro all of from one to twelve carbon atoms; halo; hydroxy; and amino; $R^9$, $R^{10}$, and $R^{11}$ are selected from hydrogen, alkyl and alkoxy of from one to twelve carbon atoms, halo and cyano; n is 0, 1, or 2; $X^1$ and $X^2$ are individually O, S, Se, or Te except that at least one of $X^1$ and $X^2$ must be Se or Te; and Z is a water-soluble anion that is inactive with respect to the cation.

3. A composition as defined in claim 1 or 2, wherein said anion is selected from the group consisting of chloride, bromide, mesylate, tetrafluoroborate, perchlorate, and hexafluorophosphate.

4. A composition as defined in claim 1, wherein said dye is selected from the group consisting of
2,6-Di-t-butyl-4-[3-(2,6-di-t-butyl-4H-telluropyran-4-ylidene)-1-propen-1-yl]selenopyrylium chloride;
2,6-Di-t-butyl-4-[3-(2,6-di-t-butyl-4H-selenopyran-4-ylidene)-1-propen-1-yl]selenopyrylium hexafluorophosphate;
2,6-Di-t-butyl-4-[3-(2,6-di-t-butyl-4H-selenopyran-4-ylidene)-1-propen-1-yl]selenopyrylium chloride;
2,6-Di-t-butyl-4-[3-(2,6-di-t-butyl-4H-telluropyran-4-ylidene)-1-propen-1-yl]thiopyrylium hexafluorophosphate;
2,6-Di-t-butyl-4-[3-(2,6-di-t-butyl-4H-telluropyran-4-ylidene)-1-propen-1-yl]thiopyrylium chloride;
2,6-Di-t-butyl-4-[3-(2,6-di-t-butyl-4H-telluropyran-4-ylidene)-1-propen-1-yl]telluropyrylium chloride;
2,6-Di-t-butyl-4-[3-(2,6-di-t-butyl-4H-telluropyran-4-ylidene)-1-propen-1-yl]pyrylium perchlorate;
2,6-Di-t-butyl-4-[3-(2,6-di-t-butyl-4H-selenopyran-4-ylidene)-3-methyl-1-propen-1-yl]telluropyrylium perchlorate;
2,6-Di-t-butyl-4-[3-(2,6-di-t-butyl-4H-selenopyran-4-ylidene)-1,3-dimethyl-1-propen-1-yl]selenopyrylium hexafluorophosphate;
2,6-Di-t-butyl-4-[3-(2,6-di-t-butyl-4H-selenopyran-4-ylidene)-1-propen-1-yl]thiopyrylium hexafluorophosphate;
2,6-Di-t-butyl-4-[3-(2,6-di-t-butyl-4H-selenopyran-4-ylidene)-1-propen-1-yl]pyrylium perchlorate;
2,6-Diphenyl-4-(2,6-diphenyl-4H-telluropyran-4-ylidenemethyl)telluropyrylium tetrafluoroborate;
2,6-Diphenyl-4-[1-(2,6-diphenyl-4H-telluropyran-4-ylidene)ethyl]telluropyrylium hexafluorophosphate;
2,6-Di-t-butyl-4-(2,6-di-t-butyl-4H-telluropyran-4-ylidenemethyl)telluropyrylium chloride;
2,6-Di-t-butyl-4-[1-(2,6-di-t-butyl-4H-telluropyran-4-ylidene)ethyl]telluropyrylium chloride;
2,6-Di-t-butyl-4-(2,6-di-t-butyl-4H-telluropyran-4-ylidenemethyl)telluropyrylium bromide;
2,6-Di-t-butyl-4-[3-cyano-3-(2,6-di-t-butyl-4H-telluropyran-4-ylidene)-1-propen-1-yl]telluropyrylium tetrafluoroborate;
2,6-Di-phenyl-4-[5-(2,6-di-phenyl-4H-telluropyran-4-ylidene)-1,3-pentadien-1-yl]telluropyrylium tetrafluoroborate;
2,6-Di-t-butyl-4-(2,6-di-t-butyl-4H-thiopyran-4-ylidenemethyl)-3-iodo-telluropyrylium hexafluorophosphate; and
2,6-Di-(4-hydroxy-n-butyl)-4-(2,6-di-t-butyl-4H-selenopyran-4-ylidenemethyl)telluropyrylium hexafluorophosphate.

5. A composition as defined in claim 1, wherein said carrier comprises an ethanol solution diluted with phosphate-buffered saline.

6. A method of increasing the survival time of animals affected with glioma or mammary carcinoma cells, comprising parentally administering to such an animal having glioma or mammary carcinoma cancer cells, a therapeutically effective amount of a seleno- or a telluropyrylium dye having a singlet oxygen quantum efficiency of at least 0.006, when exposed in an air-saturated solution to light of wavelengths between about 650 to 1000 nm with an energy sufficient to produce a phototherapeutic effect; and a pharmaceutically acceptable carrier;
and irradiating the site of said cancer cells with light at said wavelengths and with said energy levels.

7. A method as defined in claim 6, wherein said dye has the following structural formula:

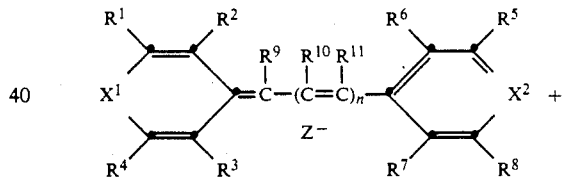

wherein $R^1$, $R^4$, $R^5$, and $R^8$ are selected from hydrogen, aryl, or alkyl from one to twelve carbon atoms; $R^2$, $R^3$, $R^6$, and $R^7$ are selected from hydrogen, alkyl, aryl, alkylthio, arylthio, alkoxy; alkylseleno, arylseleno, alkyltelluro or aryltelluro all of from one to twelve carbon atoms; halo; hydroxy; and amino; $R^9$, $R^{10}$, and $R^{11}$ are selected from hydrogen, alkyl and alkoxy of from one to twelve carbon atoms, halo and cyano; n is 0, 1, or 2; $X^1$ and $X^2$ are individually O, S, Se, or Te except that at least one of $X^1$ and $X^2$ must be Se or Te; and Z is a water-soluble anion that is inactive with respect to the cation.

8. A method as defined in claim 6 or 7, wherein said dye is selected from the group consisting of
2,6-Di-t-butyl-4-[3-(2,6-di-t-butyl-4H-telluropyran-4-ylidene)-1-propen-1-yl]selenopyrylium chloride;
2,6-Di-t-butyl-4-[3-(2,6-di-t-butyl-4H-selenopyran-4-ylidene)-1-propen-1-yl]selenopyrylium hexafluorophosphate;
2,6-Di-t-butyl-4-[3-(2,6-di-t-butyl-4H-selenopyran-4-ylidene)-1-propen-1-yl]selenopyrylium chloride;
2,6-Di-t-butyl-4-[3-(2,6-di-t-butyl-4H-telluropyran-4-ylidene)-1-propen-1-yl]thiopyrylium hexafluorophosphate;

2,6-Di-t-butyl-4-[3-(2,6-di-t-butyl-4H-telluropyran-4-ylidene)-1-propen-1-yl]thiopyrylium chloride;
2,6-Di-t-butyl-4-[3-(2,6-di-t-butyl-4H-telluropyran-4-ylidene)-1-propen-1-yl]telluropyrylium chloride;
2,6-Di-t-butyl-4-[3-(2,6-di-t-butyl-4H-telluropyran-4-ylidene)-1-propen-1-yl]pyrylium perchlorate;
2,6-Di-t-butyl-4-[3-(2,6-di-t-butyl-4H-selenopyran-4-ylidene)-3-methyl-1-propen-1-yl]telluropyrylium perchlorate;
2,6-Di-t-butyl-4-[3-(2,6-di-t-butyl-4H-selenopyran-4-ylidene)-1,3-dimethyl-1-propen-1-yl]selenopyrylium hexafluorophosphate;
2,6-Di-t-butyl-4-[3-(2,6-di-t-butyl-4H-selenopyran-4-ylidene)-1-propen-1-yl]thiopyrylium hexafluorophosphate;
2,6-Di-t-butyl-4-[3-(2,6-di-t-butyl-4H-selenopyran-4-ylidene)-1-propen-1-yl]pyrylium perchlorate;
2,6-Diphenyl-4-(2,6-diphenyl-4H-telluropyran-4-ylidenemethyl)telluropyrylium tetrafluoroborate;
2,6-Diphenyl-4-[1-(2,6-diphenyl-4H-telluropyran-4-ylidene)ethyl]telluropyrylium hexafluorophosphate;
2,6-Di-t-butyl-4-(2,6-di-t-butyl-4H-telluropyran-4-ylidenemethyl)telluropyrylium chloride;
2,6-Di-t-butyl-4-[1-(2,6-di-t-butyl-4H-telluropyran-4-ylidene)ethyl]telluropyrylium chloride;
2,6-Di-t-butyl-4-(2,6-di-t-butyl-4H-telluropyran-4-ylidenemethyl)telluropyrylium bromide;
2,6-Di-t-butyl-4-[3-cyano-3-(2,6-di-t-butyl-4H-telluropyran-4-ylidene)-1-propen-1-yl]telluropyrylium tetrafluoroborate;
2,6-Di-phenyl-4-[5-(2,6-di-phenyl-4H-telluropyran-4-ylidene)-1,3-pentadien-1-yl]telluropyrylium tetrafluoroborate;
2,6-Di-t-butyl-4-(2,6-di-t-butyl-4H-thiopyran-4-ylidenemethyl)-3-iodo-telluropyrylium hexafluorophosphate; and
2,6-Di-(4-hydroxy-n-butyl)-4-(2,6-di-t-butyl-4H-selenopyran-4-ylidenemethyl)telluropyrylium hexafluorophosphate.

9. A composition as defined in claim 1, wherein said dye is 2,6-di-t-butyl-4-[3-(2,6-di-t-butyl-4H-telluropyran-4-ylidene)-1-propen-1-yl]selenopyrylium chloride.

10. A method as defined in claim 6, wherein said dye is 2,6-di-t-butyl-4-[3-(2,6-di-t-butyl-4H-telluropyran-4-ylidene)-1-propen-1-yl]selenopyrylium chloride.

* * * * *